United States Patent
Lee et al.

(10) Patent No.: US 8,941,487 B2
(45) Date of Patent: Jan. 27, 2015

(54) TRANSFERRING A MOBILE TAG USING A LIGHT BASED COMMUNICATION HANDSHAKE PROTOCOL

(71) Applicant: Salutron, Inc., Fremont, CA (US)

(72) Inventors: Yong Jin Lee, Palo Alto, CA (US); Chor Kuen Eddy Hui, Kowloon (HK)

(73) Assignee: Salutron, Inc., Fremont, CA (US)

( * ) Notice: Subject to any disclaimer, the term of this patent is extended or adjusted under 35 U.S.C. 154(b) by 132 days.

(21) Appl. No.: 13/789,667

(22) Filed: Mar. 7, 2013

(65) Prior Publication Data

US 2013/0234850 A1    Sep. 12, 2013

Related U.S. Application Data (60) Provisional application No. 61/609,136, filed on Mar. 9, 2012, provisional application No. 61/749,465, filed on Jan. 7, 2013, provisional application No. 61/749,913, filed on Jan. 8, 2013, provisional application No. 61/848,644, filed on Jan. 7, 2013.

(51) Int. Cl.

| | |
|---|---|
| G08B 1/08 | (2006.01) |
| G06F 19/00 | (2011.01) |
| A61B 5/02 | (2006.01) |
| H04B 10/114 | (2013.01) |
| A61B 5/00 | (2006.01) |
| A61B 5/107 | (2006.01) |

(52) U.S. Cl.
CPC .............. *G06F 19/3418* (2013.01); *A61B 5/02* (2013.01); *H04B 10/114* (2013.01); *A61B 5/6898* (2013.01); *A61B 5/107* (2013.01); *A61B 5/0015* (2013.01); *A61B 5/681* (2013.01); *H04B 10/1143* (2013.01)
USPC ................. 340/539.12; 340/539.1; 340/573.1

(58) Field of Classification Search
None
See application file for complete search history.

(56) References Cited

U.S. PATENT DOCUMENTS

| 5,508,690 | A  * | 4/1996 | Shur et al. ...................... 340/505 |
| 7,030,773 | B2 * | 4/2006 | Peterson et al. ........... 340/815.4 |
| 8,092,393 | B1 * | 1/2012 | Rulkov et al. ................. 600/503 |

(Continued)

FOREIGN PATENT DOCUMENTS

WO        2009032522 A1    3/2009

OTHER PUBLICATIONS

International Search Report and Written Opinion dated Jul. 16, 2013 in International Patent Application No. PCT/US2013/030010, 10 pages.

*Primary Examiner* — Travis Hunnings
(74) *Attorney, Agent, or Firm* — Vierra Magen Marcus LLP (57) ABSTRACT

Technology is described for transferring one or more mobile tags using a light based communication protocol. A mobile device, for example a smart phone, with an image sensor and an illuminator, like a camera flash, initiates transfer of data formatted in a mobile tag displayed by another device by automatically controlling the illuminator to generate sequences of light representing data transfer messages. The other device, for example a user wearable computer device with sensors capturing biometric and health related data, has a photodetector unit for capturing the sequences of light and converting them into digital data. A processor of the other device identifies the data transfer messages and causes a display of one or more mobile tags responsive to the messages. In this way, a number of mobile tags may be used to transfer several kilobytes of biometric data, for example 4-7 KBs, using low power for the wearable device.

20 Claims, 8 Drawing Sheets

(56) References Cited

U.S. PATENT DOCUMENTS

| | | |
|---|---|---|
| 2005/0231381 A1* | 10/2005 | Pederson et al. ......... 340/815.45 |
| 2006/0052055 A1 | 3/2006 | Rowse et al. |
| 2008/0136661 A1* | 6/2008 | Pederson et al. ......... 340/815.45 |
| 2011/0069974 A1* | 3/2011 | Kim et al. .................... 398/200 |
| 2014/0173289 A1* | 6/2014 | Casilli .......................... 713/185 |

* cited by examiner

TRANSFERRING A MOBILE TAG USING A LIGHT BASED COMMUNICATION HANDSHAKE PROTOCOL

CROSS-REFERENCE TO RELATED APPLICATIONS

This application claims priority under 35 USC Section 119(e) to the following provisional applications U.S. provisional application No. 61/609,136 to Lee et al. filed Mar. 9, 2012 entitled "Communications Link Between Health Monitor and Mobile Computing Device," U.S. provisional application No. 61/749,465 to Lee et al. filed Jan. 7, 2013 entitled "Communications Link Between Health Monitor and Mobile Computing Device," U.S. provisional application No. 61/749,913 to Lee et al. filed Jan. 8, 2013 entitled "Communications Link Between Health Monitor and Mobile Computing Device," and U.S. provisional application No. 61/848,644 to Lee et al. filed Jan. 7, 2013 entitled "Communications Link Between Health Monitor and Mobile Computing Device," all of which are hereby incorporated by reference.

BACKGROUND OF THE INVENTION

1. Field of the Invention

The present invention relates to wireless communications.

2. Description of the Related Art

There are various devices that can be used to monitor the health of a person or animal. An example of such a device is a heart rate monitor in a wrist watch form as described in U.S. Pat. No. 6,843,771 entitled "Ultrasonic Monitor for Measuring Heart Rate and Blood Flow Rate" to Lo et al., issued Jan. 18, 2005 and assigned to Salutron, Inc. A user wearable computer device may also collect data from other types of sensors such as accelerometer data which can provide data on speed for applications such as pedometers and calorie counting. The biometric data captured by health monitoring devices can be used by various applications on a mobile computing device, also referred to as a mobile computer device such as a smart phone, or uploaded over a network to a remote computer system for further analysis and tracking of the user's biometric data.

Health monitoring sensors typically have contact with the skin and are often placed at various joints of the body such as the wrist or ankle for better capture of pertinent data rather than being supported in a back pack on a person's back. A user wearable health monitoring computer device also has to have a battery that is comfortable to wear by a human and also does not drain too quickly. It can be challenging to communicate the biometric data from a user wearable health monitoring computer device to a mobile computer device in an efficient and cost effective manner.

SUMMARY

The technology provides for transferring one or more mobile tags between computer devices using a light based communication handshake protocol.

The technology provides one or more embodiments of a method for transferring one or more mobile tags using a light based communication handshake protocol. An embodiment of the method comprises capturing image data of an electronically displayed mobile tag with an image sensor of a mobile computer device. A successful read of data encoded in the mobile tag is identified, and based on the data encoded in the mobile tag, it is identified whether the mobile tag is the last mobile tag of data in a series. Responsive to the mobile tag not being the last mobile tag of data in the series, a sequence of light flashes is generated with an illuminator of the mobile computer device in accordance with a communication handshake protocol for indicating to display a next mobile tag. Responsive to the mobile tag being the last mobile tag of data in the series, the display of the mobile computer device is updated to indicate an end of data transfer for the user.

The technology provides one or more embodiments of a system for transferring one or more mobile tags using a light based communication handshake protocol. An embodiment of the system comprises a mobile device including a processor, a memory storing software and data and being accessible by the processor, as well as an image sensor and an illuminator both communicatively coupled to the processor. The mobile device further comprises one or more user input devices from which the processor under control of the software receives user input indicating a request for transfer of data from another computer device. The processor under control of the software causes the image sensor to be turned on and causes the illuminator to generate a sequence of light flashes indicating a message requesting transfer of the data in accordance with a communication handshake protocol.

The processor under control of the software identifies a mobile tag in image data being captured by the image sensor, and extracts data encoded in the mobile tag. Responsive to the data extracted from the mobile tag indicating there is more data to be transferred, the processor causes the illuminator to generate a sequence of light flashes indicating a message to display another mobile tag encoded with data.

Another embodiment of the technology comprises a user wearable biometric sensing computer device for communicating biometric data to a mobile computer device. The user wearable biometric sensing computer device further comprises a processor, a display communicatively coupled to the processor, one or more biometric sensing units for generating biometric data communicatively coupled to the processor, a memory accessible by the processor for storing software and the biometric data, and a photodetector unit communicatively coupled to the processor which unit captures one or more sequences of light flashes, and converts the one or more sequences of light flashes into digital data, and stores the digital data in the memory.

The processor identifies one or more messages in the digital data based on a communication handshake protocol for the one or more sequences of light flashes, and controls displaying of the biometric data formatted in one or more mobile tags in accordance with a mobile tag code on the display based on the one or more messages identified in the one or more sequences of light flashes. A user wearable support structure supports the processor, the display, the memory, the one or more biometric sensing units and the photodetector unit.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

The technology provides for a low power transfer of data based on a communication handshake protocol in which sequences of light flashes representing messages are detected by a photodetector of a device, particularly a low power computer device like a user wearable biometric sensing device. The photodetector converts the photons of the light flashes to electrical signals which are then converted from analog to digital form as digital data, e.g. bit values of "1"s and "0"s, from which a processor of the computer device having the photodetector identifies data transfer messages like start and next. The computer device receiving the light flashes responds by displaying one or more mobile tags of data which a mobile computer device, for example, a smart phone, generating the light flashes captures with its image sensor, for example its camera, and extracts the data in each tag using mobile tag recognition technology.

As described further below, a user wearable biometric sensing computer device may be embodied as a wrist wearable computer device with a watch like unit housing and supporting the computer hardware and software, biometric sensors, and providing a watch like display. In some examples, biometric data based on sensor readings from the various sensors such as heart rate and blood flow sensors or accelerometers may be transferred in the mobile tags. Depending on an application, several kilobytes KB of data may be transferred in a session, for example 4-7 KB. In an example where each mobile tag can encode about 1 KB, a secession of mobile tags may be displayed on the watch like display. The communication handshake allows the mobile device recognizing the mobile tag to communicate when to send the next tag and can acknowledge no errors or indicate an error occurred to the user wearable device. In some embodiments, the computer device encoding the mobile tag encodes a symbol, character or other representation indicating this is the last tag of data.

Some examples of mobile tagging codes are QR-Code, DataMatrix, Cool-Data-Matrix, Aztec, Upcode, Trillcode, Quickmark, Shotcode, mCode and Beetagg which are also examples of two dimensional (2D) barcodes which a mobile device with the corresponding 2D barcode reader software installed can read. Another type of mobile tag which uses color rather than black and white squares is Microsoft's° High Capacity Color Barcode (HCCB) standard. Some of these codes encode data redundantly to account for perspective and glare issues. In some embodiments, to save on size of data to be transferred, redundant encoding of data may be omitted.

Figure 1:
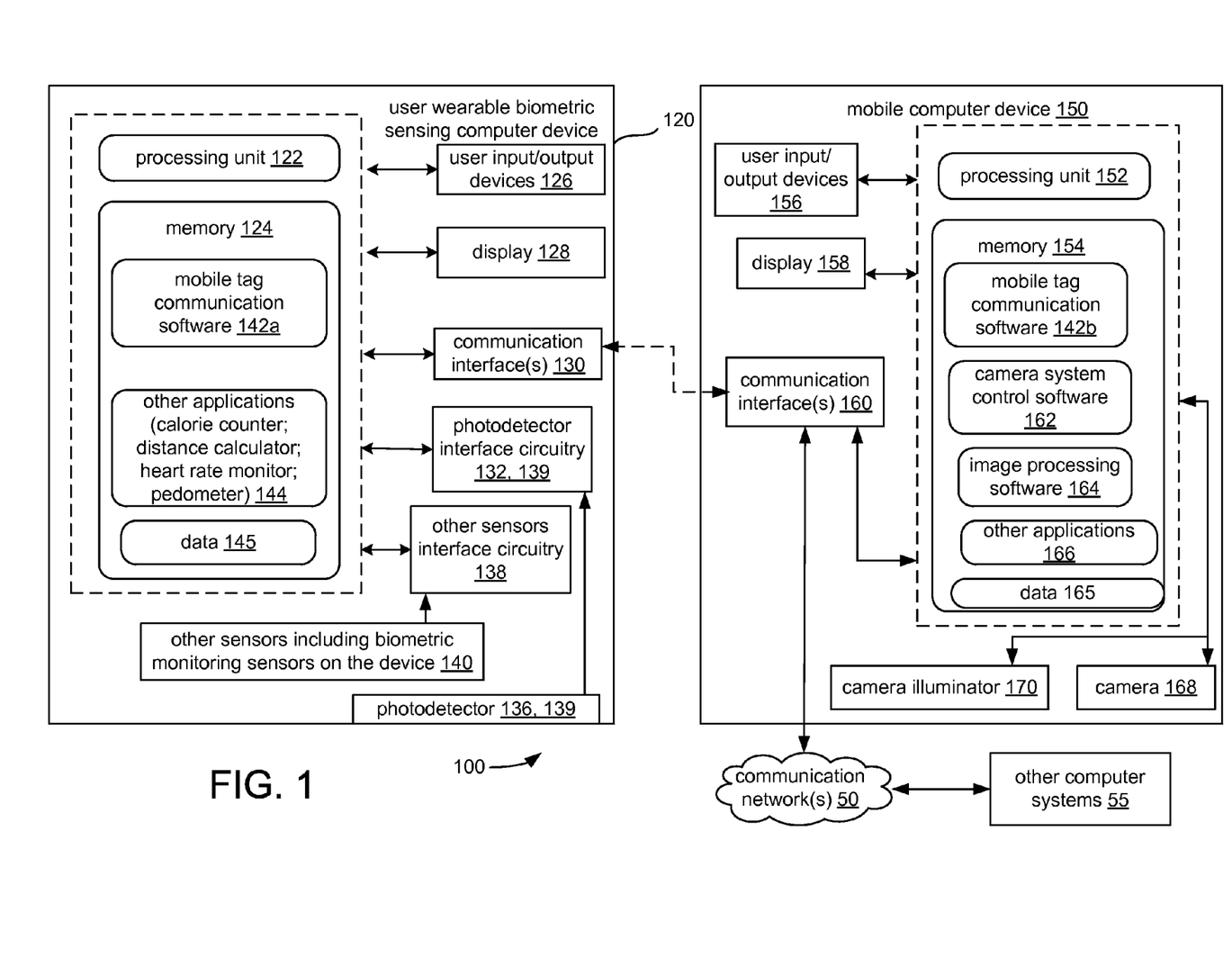
FIG. 1 illustrates one or more examples of computer devices for use in an embodiment of a system for transferring one or more mobile tags using a light based communication handshake protocol.

FIG. 1 illustrates one or more examples of computer devices for use in an embodiment of a system for transferring one or more mobile tags using a light based communication handshake protocol. A computing device or a computer device is a device having at least one processor and a memory. In this example, two exemplary mobile or portable computer devices are illustrated, a user wearable biometric sensing computer device 120 and a mobile computer device 150.

Each device 120, 150 has a respective processing unit 122, 152 with one or more processors, communicatively coupled to a respective display 128, 158, respective user input devices 126, 156 and respective communication interfaces 130, 160 for communicating over wire or wirelessly with other computer systems to which they may be networked. A computer system may be embodied in one or more computer devices. A respective memory 124, 154 which may provide both non-volatile and volatile storage is accessible by its respective processing unit 122, 152 and other components like its respective display and communication interfaces. Memory 124 is also accessible to interface circuitry 132 for the photodetector and interface circuitry 138 for other sensors for buffering and/or storing of their digital data readings. Memory 124 stores data 145 which may include user profile data, sensor and photodetector digital data readings, reference data transfer messages for identifying by comparison whether the digital data contains a data transfer message, and data generated during runtime and for storage by the various software applications stored including a mobile tag communication software application 142a. Examples of other applications 144 which may be stored are also illustrated with biometric related type of applications. Additionally, a mobile tag generator for a mobile tag code may be stored in the other applications 144.

Memory 154 in the mobile device 150 is also accessible to an image sensor embodied as a camera 168 for buffering and storing of image data. Memory 154 stores data 165 some examples of which may include user profile data, captured image data as mentioned, images, moving or still, and text as visual aids (discussed further below) and data generated during runtime and for storage by the various software applications stored. A mobile tag communication software application 142b for a mobile tag reading device, a camera system control software application 162, and image processing software 164 are stored as well as other applications 166. Each of the memories 124 and 154 are examples of processor readable storage devices which fix data in place for reading and writing.

The complexity of the architecture components vary. For example, for an embodiment of the user wearable biometric sensing computer device as a wrist watch with a display 128, the user input and output devices 126 may include small buttons, e.g. on the side of the watch, the top of the watch, and display 128 may also be an input device by being a touch sensitive display 128 which may be activated with a stylus or finger in some embodiments. Output devices 126 other than the display 128 may include a beeping device. The memory 154, processing capability of the processing unit 152, communication interface 160 wireless range and number of connections supported, as well as quality of display on the display 158, and sound quality of speakers as audio output devices 156 of the mobile computer device 150 very likely substantially exceed that of the biometric sensing computer device 120 in this example which prioritizes being light weight and low power.

An example of a communication interface(s) 130 of the biometric sensing computer device 120 may be a type of USB port, a Bluetooth port, or an IR port. Some examples of communication interface(s) 160 on the mobile computer device 150 are a USB port, a cellular network connection and a WiFi wireless connection which allow the mobile computer device 150 to communicate over one or more communication network(s) 50 with other computer systems 55. Some examples of a communication network 50 are a local area network and the Internet. As illustrated by the dashed arrow in some embodiments, the devices 120, 150 may also communicate using a Bluetooth, IR or other wireless/wired connection.

The user wearable biometric sensing computer device 120 also has sensor interface circuitry 138 for other sensors besides the photodetector 136 which other sensors include biometric monitoring sensors which provide the data from which calories, heart rate, distance walked and the like can be determined for requesting applications, some of which may execute locally such as the illustrated examples of other applications 144, a calorie counter application, a distance calculator, a heart rate monitor application, and a pedometer application. The photodetector 136 on the wearable device also sends its signals to a photodetector interface circuitry 132, and together they provide a photodetector unit 139 which detects and converts flashes of light into electrical signals which the photodetector interface circuitry 132 converts to digital data readable by a processor of the processing unit 122.

The photodetector 136 may is sensitive to light including the wavelength of light of the camera illuminator 170. In some examples, the photodetector detects peaks and valleys or highs and lows of light intensity as the camera illuminator 170 placed over the photodetector 136 generates flashes of light. These highs and lows may be correlated to be bit values of 0's and 1's and sequences of these bit values can represent messages. A serial communication protocol may be used to implement the handshake. An example of an analogous communication handshake protocol using messages for asynchronous communication with a handshake is the RS-232 handshake protocol. Another example of an analogous protocol is Universal Asynchronous Retriever Transmitter (UART). In one version of the protocol, a bit value of one is represented by a detection of the light flash as represented by its intensity, and a bit value of zero is represented by an intervening time period of not detecting light at the intensity of the light flash. In other words, an on and off sequence of flashes can represent one or more bits or other values. In other embodiments, the communication protocol can represent higher level values, for example, 0 to F in hexadecimal. For example, the communication protocol may use a time period at a certain level of light intensity to represent a bit value and a time period at a lower level of light intensity to represent another bit value if the camera illuminator allows variation in the light flash intensity. In other examples, the light intensity of the camera illuminator light flashes varies to indicate more than two values. Also, the time periods for different intensity values may be varied as well to indicate different values in other examples, and the intensity values and time periods may also be varied for representing different values The mobile computer device 150 includes an embodiment of an image sensor as a camera 168, and includes as an illuminator, a camera illuminator 170, often referred to as a camera flash. As illustrated in the memory 154, the mobile device 150 includes camera system control software 162 with which an executing version of a mobile tag communication software application 142b for a data reader computer device can communicate, for example, through an application programming interface (API). The application 142b communicates via the camera control software 162 for automatically controlling light flash generation by the camera illuminator 170 in accordance with the communication handshake protocol. The application 142b may also interact with the camera control software 162 for receiving notice that image data has been captured and its buffer location. The mobile tag communication software 142b may include or interface with a mobile tag reader application (e.g. 166) for identifying a mobile tag. One or more standard mobile tag reader applications may be included or interfaced with, or the mobile tag reader software can be customized, for example to avoid the use of redundant data or to identify a customized tag appearance for display dimensions of a device.

The mobile tag communication software application 142b may also have performed real-time transformations necessary for perspective, scaling and orientation or rotation issues. For example, special symbols in the tag are identified from which a transformation matrix can be derived for reorienting and resizing an image and determining if all of a 2D bar code displayed in a tag was captured in the image data. The application 142b may also have performed symbol or character recognition.

The mobile tag communication software application 142b can also communicate with the image processing software 164 for identifying camera related issues such as focus correction need, blur levels, glare detection and other image processing functionality provided by digital cameras generally.

Additionally, the image processing software 164 can be used to identify the user wearable computer device 120 in image data based on pattern recognition with one or more reference images stored in memory. In some embodiments, the image processing software 164 can generate an outline version image of an object in which an outline of a perimeter of an object appears while the rest of the object appears to be see-through. Contrast ratio can be turned to extremes or edges isolated using edge detection software. In other examples, the outline version image, which can be used as a visual alignment aid, is generated offline for different models of tag generator devices like the user wearable biometric sensing computer device and downloaded over a communication network 50 by the mobile tag communication software 142b.

The user wearable biometric sensing computer device 120 includes a data generator version of the mobile tag communication software application 142a. The software identifies messages in the digital data generated by the photodetector based on a communication handshake protocol. Additionally, the mobile tag communication software application 142a includes a mobile tag encoder or interfaces with mobile tag generation software, for example, mobile tag generation software for a standard mobile tag code. In some cases, the mobile tag generator may modify a standard tag or use its own custom version, for example, to avoid encoding redundant data to speed the data transfer as a user may be holding the mobile device near the sensing computer device. The mobile tag communication software 142a formats the generated mobile tag for display on its device's 120 display 128 and causes each tag to be displayed responsive to messages like start, next, send or display, re-send or re-display identified from the light flashes detected by the photodetector 136. Each tag may have an identifier code and a sequence number in its data to assist the data reader version of the software 142b to track which tags in a series of tags have been received and read successfully, and which had errors for resending.

Figure 2A:
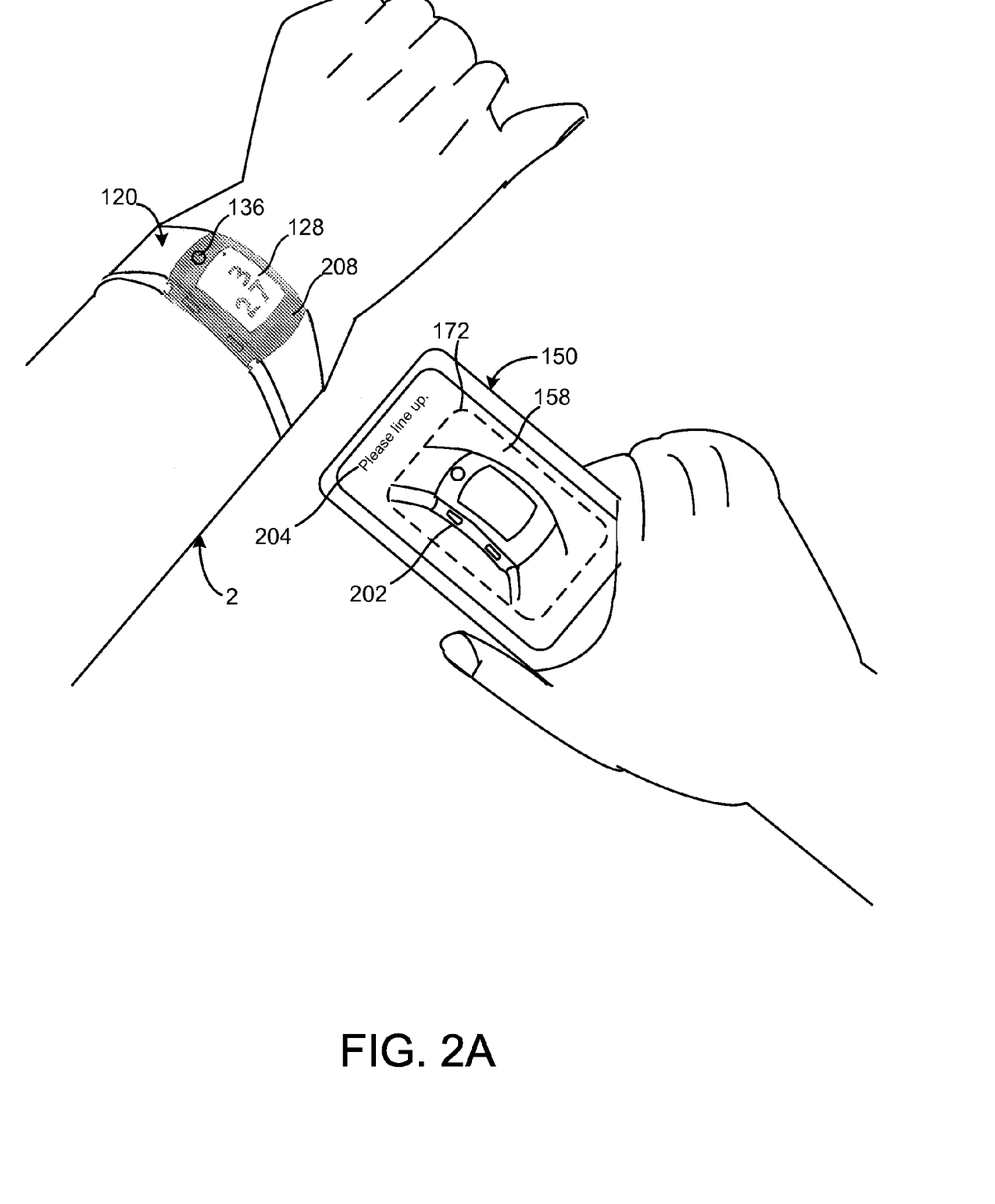
FIGS. 2A and 2B illustrate examples of visual aids for assisting a user in positioning an example of a user wearable computer device in a wrist watch form in a field of view of an image sensor of a mobile device.
Figure 2B:
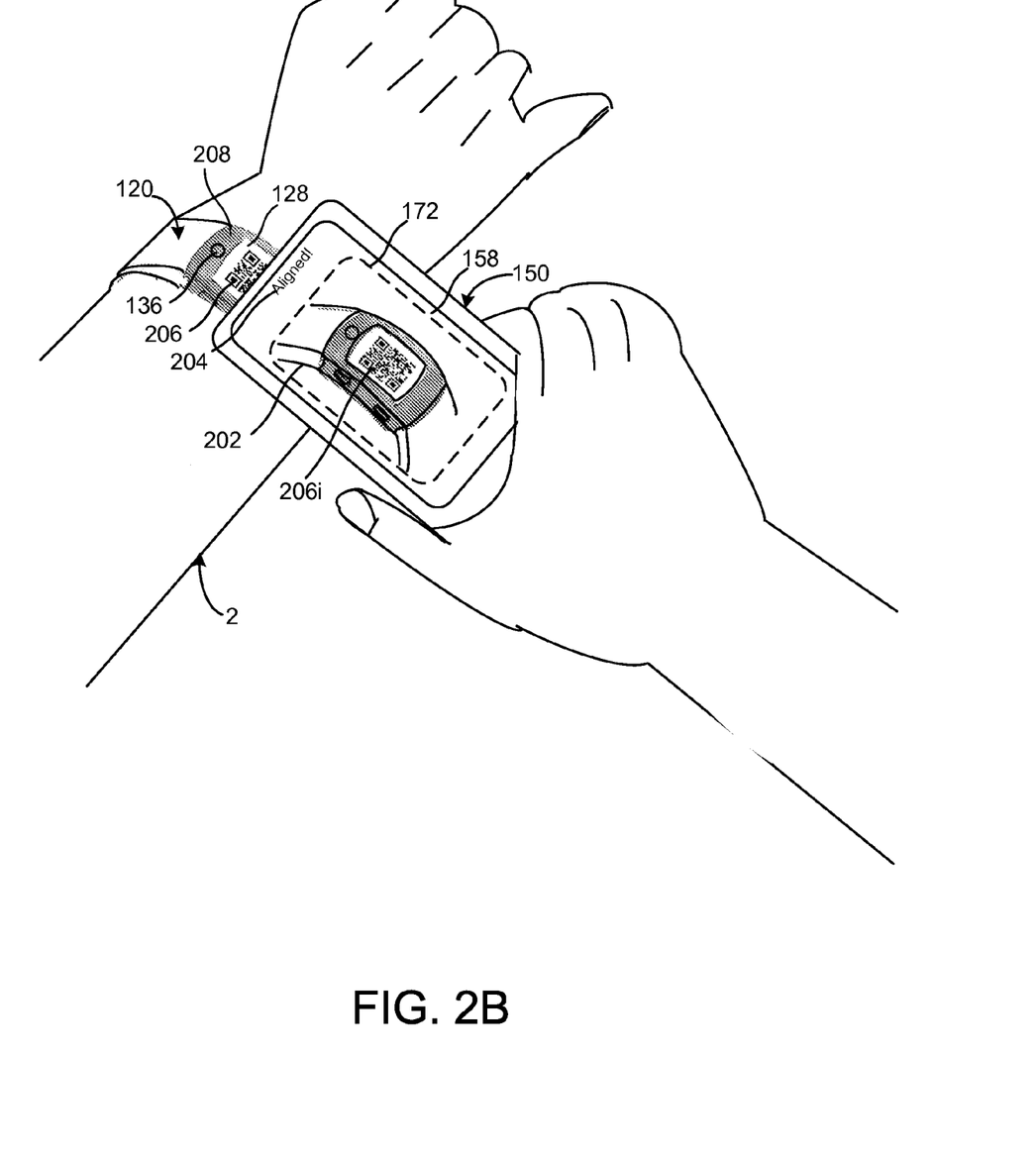

FIGS. 2A and 2B illustrate examples of visual aids for assisting a user in positioning an example of a user wearable computer device in a wrist watch form in a field of view of an image sensor of a mobile device.

In the contextual example of FIG. 2A, a user 2 is wearing the biometric sensing device 120 embodied in a wrist watch form factor 208 with its watchface display 128 illustrating heartbeat data and photodetector 136 on the face of the watch above the display. In other embodiments, the photodetector 136 may be positioned on or within the display 128. The user is holding a mobile device 150 embodied as smartphone, and has already initiated the mobile tag communication application to start uploading data with user input (see FIG. 3A). The mobile tag communication application 142b displays instructions or position hints 204 such as "Please line up" and displays another visual aid 202 which is the outline version image for the wrist wearable biometric sensing device 120. In other examples, the alignment aid may be a simpler shape such as a rectangle or a circle. The outline version helps the user also achieve a good distance of the mobile device 150 from the display 128 which has been predetermined offline for optimal reading under certain light conditions. The outline version image 202 may be adjusted based on ambient light conditions identified in image data by the image processing software or an ambient light sensor (not shown) on the mobile device 150.

FIG. 2B continues the contextual example in which the user has successfully aligned the smartphone 150 with the outline version image 202 and over the watch display 128 as indicated by the visual indicator or visual aid 204 "Aligned". The photodetector 136 has received a sequence of light flashes indicating a request to start displaying the data and is displaying a QR code type of mobile tag 206 which is also within the field of view 172 of image sensor or camera 168 as displayed by the camera software 162 on the display 158 of the smartphone. The image data of the QR code tag or modified QR code tag will be processed for extracting the biometric data therein.

In this contextual example, an exchange of data may occur as in the following example. The first mobile tag displayed may be a set of handshake characters previously stored in the memory 124, 154 in both devices for verifying recognition quality. The wrist biometric sensing computer device 120 goes into an upload mode and displays the hand-shake characters. The phone 150 waits for the hand-shake characters, and on successful reception, the phone 150 sends an acknowledgement message via the camera illuminator 170 which is detected by the photodetector 136 on the watch face. The wrist device 120 starts with a first mobile tag of biometric data. Upon successful detection of the message characters and the data encoded therein passing a data integrity check, the phone causes the camera illuminator to send a light signal of flashes encoding a message to the watch to proceed with the next mobile tag. In the last mobile tag is included an end-of-message character. Once the phone receives the last mobile tag with the end-of-message character, the phone may have the illuminator send an end of message or end of data acknowledgement for the photodetector 136 to detect, and both devices may end the communication session or start another session for a different type of data, e.g. heart rate after calorie burn data.

The mobile device 150 may use one or more sequences of light flashes to send small amounts of data to the wearable biometric sensing device 120. For example, a person's most current weight may be downloaded for a calorie counting application. A small text message advertisement may be sent down. Additionally, the messages for the communication protocol may also include data identifying from which application data is to be uploaded and a password or authentication code which verifies permissible access to the data stored on the sensing computer device 120.

Glare may be a factor. Alignment between the camera and the watchface may be causing perspective or rotation issues, particularly if a simpler visual guide is used than the outline version image. The image data may be adjusted for perspective or rotation identified within certain ranges. The mobile tag software 142b may identify a user positioning hint for display to the user to identify to the user how to move the smartphone 150 to improve the reading of the data. A data integrity check, for example a checksum may be performed on the extracted data to verify whether errors have occurred in the data. Additionally, messages may be encoded with cyclic redundancy codes or other error correction codes.

Figure 3A:
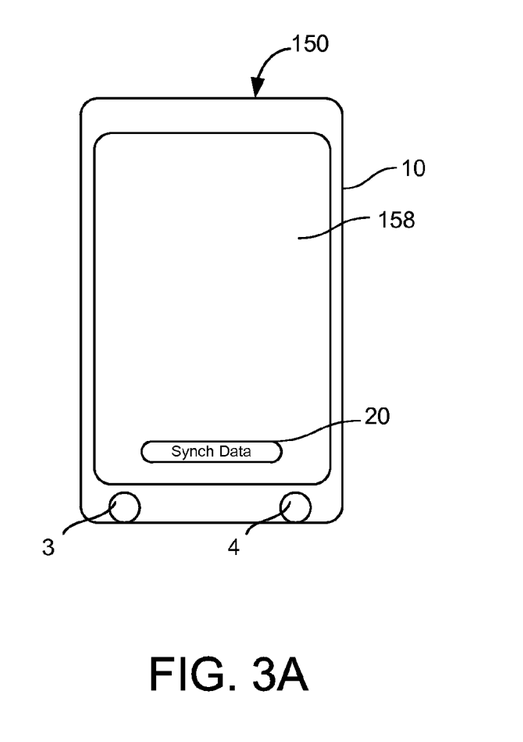
FIGS. 3A and 3B illustrate respectively a front side of a display and a back side in which is positioned a camera aperture and a camera illuminator as an exemplary mobile device which may be used in generating light flashes for a communication handshake protocol.
Figure 3B:
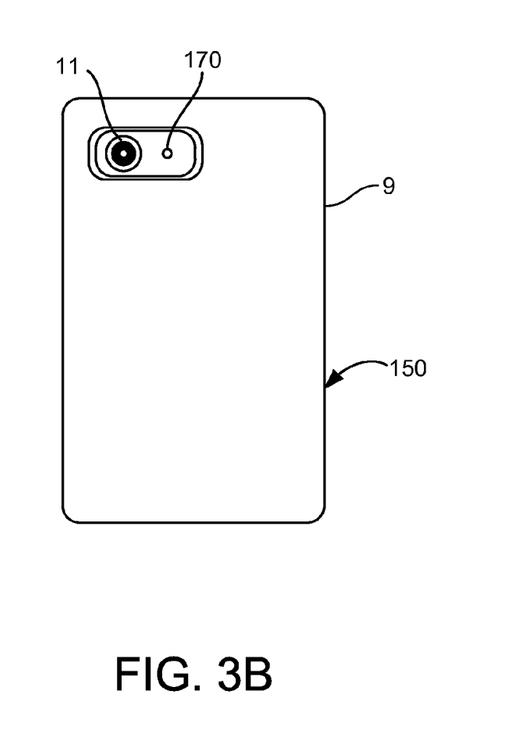

FIGS. 3A and 3B illustrate an exemplary mobile device 150. FIG. 3A illustrates the front exterior side 10 with display 158 which as a touchscreen is also a user input device. The display 158 displays a button labeled "Synch Data" which a user may press to request start of the transfer of mobile tags from another computer device like the biometric sensing device 120. Also shown are input devices of buttons 3 and 4. FIG. 3B shows the back exterior side 9 in which is positioned a camera aperture 11 and the camera illuminator 170 commonly called the camera flash. The positioning of the camera aperture 11 and illuminator 170 near each other on smartphones facilitates being able to do light based communication with a device which also fits within the camera field of view 172. The display 158 on the other side allows a user to see what the camera "sees" in real time and make position adjustments accordingly.

The technology may be embodied in other specific forms without departing from the spirit or essential characteristics thereof. Likewise, the particular naming and division of modules, routines, applications, features, attributes, methodologies and other aspects are not mandatory, and the mechanisms that implement the technology or its features may have different names, divisions and/or formats.

For illustrative purposes, the method embodiments below are described in the context of the system and apparatus embodiments described above. However, the method embodiments are not limited to operating in the system and apparatus embodiments described above and may be implemented in other system and apparatus embodiments.

Figure 4:
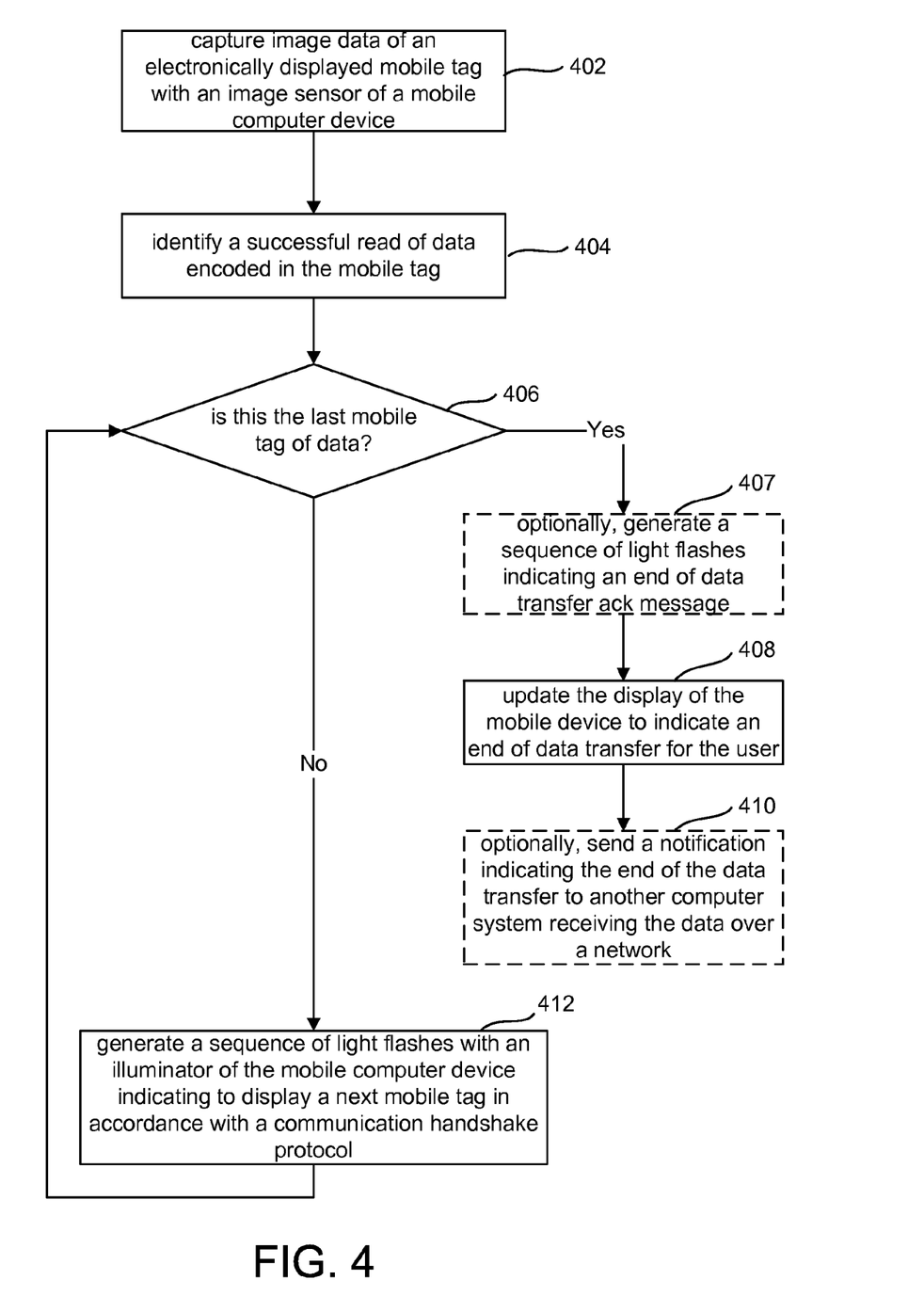
FIG. 4 is a flow chart illustrating an embodiment of a method for transferring one or more mobile tags using a light based communication handshake protocol.

FIG. 4 is a flow chart illustrating an embodiment of a method for transferring one or more mobile tags using a light based communication handshake protocol. In step 402, the mobile computer device 150 captures image data of an electronically displayed mobile tag with an image sensor of the mobile computer device, and the mobile tag communication application 142b in step 404 identifies a successful read of data encoded in the mobile tag. In step 406, the application 142b executing on one or more processors of the processing unit 152 determines whether this is the last mobile tag of data. For example, the tag data may indicate an end of data character or symbol. The end of data character may be in the last tag by itself or included with encoded data of the last tag.

Responsive to the tag being the last mobile tag of data, optionally, in step 407, the mobile tag communication application 142b may cause the camera illuminator 170 to generate a sequence of light flashes indicating an end of data transfer acknowledgement message. In step 408, the display of the mobile device 150 is updated for indicating the end of data transfer for the user so the user can move at least one of the devices. Optionally, in a case, where the data extracted from the tags or even the tags themselves are being sent to a remote computer system 55 over a network 50, in step 410, the mobile tag communication application 142b sends a notification indicating the end of the data transfer to another computer system 55 receiving over a network 50.

Responsive to the tag not being the last mobile tag of data, in step 412, the application 142b causes an illuminator 170 of the mobile computer device to generate a sequence of light flashes indicating to display a next mobile tag in accordance with a communication handshake protocol.

Figure 5A:
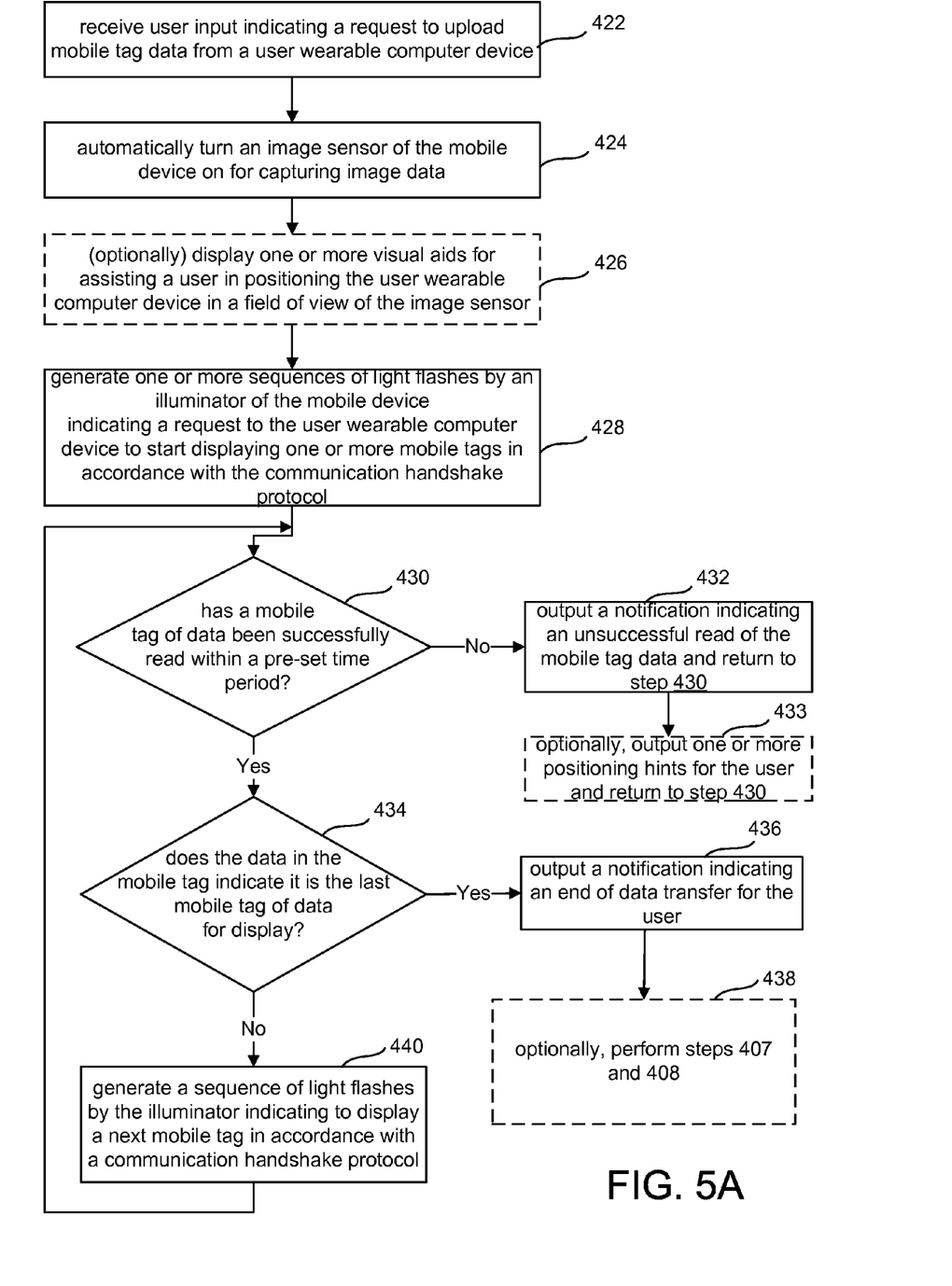
FIG. 5A is a flow chart illustrating a more detailed example of a method for transferring one or more mobile tags using a light based communication handshake protocol from a perspective of a hand held mobile computer device with an image sensor and an illuminator.

FIG. 5A is a flow chart illustrating a more detailed example of a method for transferring one or more mobile tags using a light based communication handshake protocol from a perspective of a hand held mobile computer device with an image sensor and an illuminator. Besides smartphones, some other examples of mobile devices which can also be hand held are digital cameras, tablet computers, small or mini tablet computers, and messaging devices with cameras and camera flashes.

In step 422, the mobile device 150 receives user input indicating a request to upload mobile tag data from a user wearable computer device (e.g. 120) and notifies the mobile tag communication application 142b which in step 424 causes the camera software 162 to automatically turn an image sensor 168 of the mobile device on for capturing image data.

Optionally, in step 426, one or more visual aids is displayed for assisting a user in positioning the user wearable computer device in a field of view of the image sensor. The mobile communication tag application 142b via the camera software 162 in step 428, generates one or more sequences of light flashes by an illuminator of the mobile device which one or more sequences indicate a request to the user wearable computer device to start displaying one or more mobile tags in accordance with the communication handshake protocol.

In step 430, it is determined whether a mobile tag of data has been successfully read within a pre-set time period. As noted in an example above, there may be an initial exchange of predetermined handshake characters stored at both devices to verify a mobile tag can be read. Additionally, a checksum or other error checking or data integrity checking scheme may be applied to the data extracted from the tag to verify whether an error has occurred or not.

Responsive to an unsuccessful read, in step 432 a notification is output indicating an unsuccessful read of the mobile tag data via audio data, visual data on the mobile device display or both and the determination in step 430 is periodically performed until either a successful read or the user exits the application. Optionally, in step 433, one or more positioning hints are output to the user in audio data, visual data or both and the determination in step 430 is periodically performed until either a successful read or the user exits the application.

Responsive to a successful read, in step 434, the application 142b determines whether the data in the mobile tag indicates it is the last mobile tag of data for display. Responsive to the tag being the last tag of data, in step 436, a notification indicating an end of data transfer is output to the user. Optionally, steps 407 and 410 may be performed as well.

Responsive to the tag not being the last mobile tag of data, in step 440 a sequence of light flashes is generated by the illuminator indicating to display a next mobile tag in accordance with a communication handshake protocol.

Figure 5B:
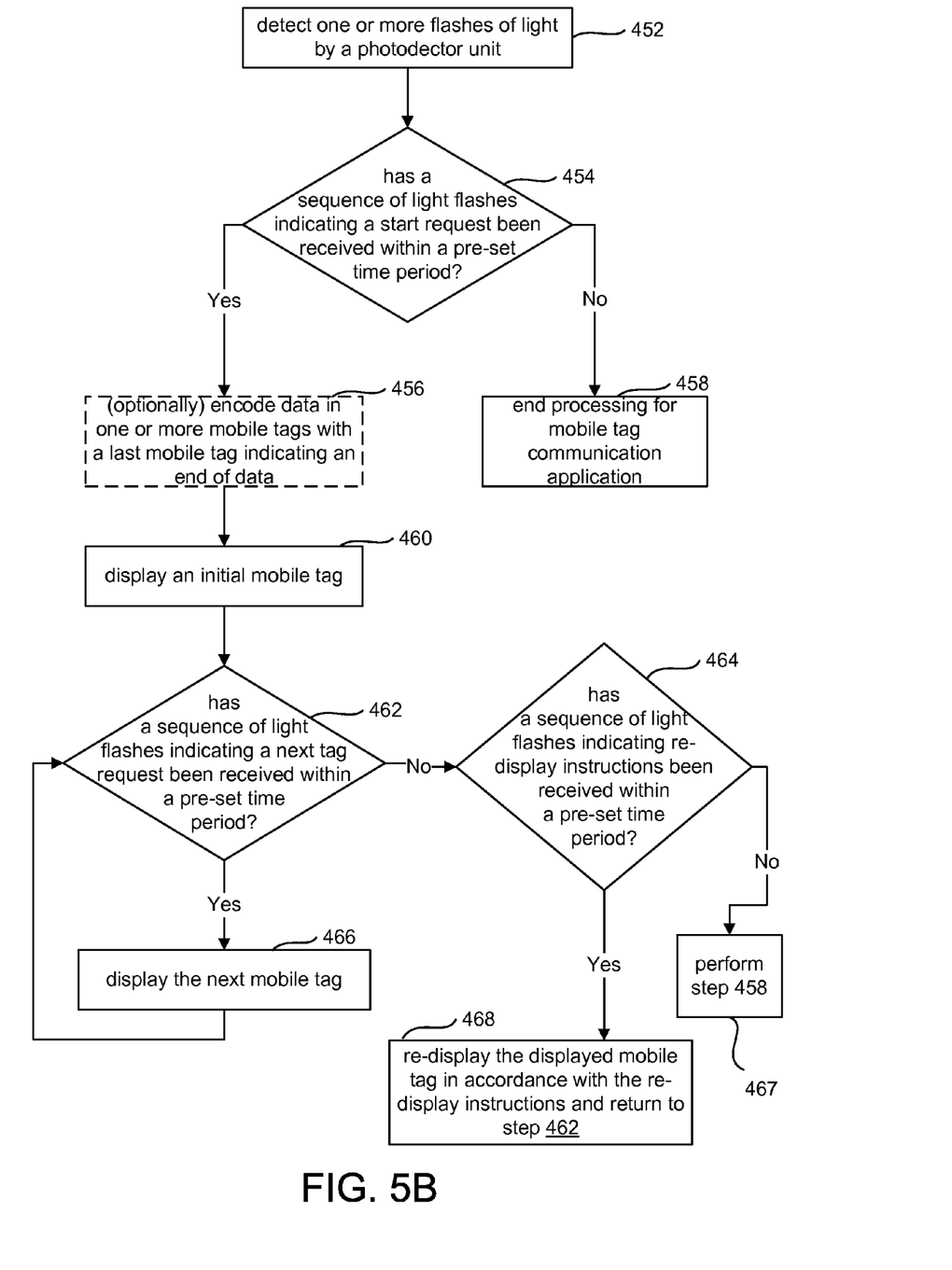
FIG. 5B is a flow chart illustrating a more detailed example of a method for transferring one or more mobile tags using a light based communication handshake protocol from a perspective of a user wearable computer device which displays one or more mobile tags in accordance with the handshake protocol.

FIG. 5B is a flow chart illustrating a more detailed example of a method for transferring one or more mobile tags using a light based communication handshake protocol from a perspective of a user wearable computer device which displays one or more mobile tags in accordance with the handshake protocol. In step 452, a photodetector unit detects one or more flashes of light which are converted to digital data and a notification is sent to the mobile tag communication application 142a which reviews digital data being received by the photodetector for determining in step 454 whether a sequence of light flashes indicating a start request has been received within a pre-set time period. If the sequence indicating the start request has not been received within the pre-set time period, the mobile tag communication application ends its processing. The one or more flashes of light may have been a false positive, for example, a flash of light caused by reflection off a passing car.

Responsive to the start request being indicated by the sequence of light flashes within the pre-set time period, optionally, in step 456 the data such as biometric data for transfer may be encoded at this point in one or more mobile tags with a last mobile tag indicating an end of data. In other examples, the biometric data may be continuously encoded in mobile tags and stored as memory permits prior to a data transfer session with a mobile device. In other examples, the data may be encoded in a respective tag after a successful read of a previous tag. In step 460, an initial mobile tag is displayed. In step 462, it is determined whether a sequence of light flashes indicating a next tag request has been received within a pre-set time period. If so, in step 466, the mobile tag communication application 142a causes the next mobile tag to be displayed and returns to step 462 to wait for another message or time out of the pre-set time period.

If a message indicating a next tag request is not received in the pre-set time period, the mobile tag transfer application 142a in step 464 determines whether a sequence of light flashes indicating re-display instructions has been received within a pre-set time period. If not, in step 467, the application 142a may save the current location of data not yet transferred and release the processor and display for other applications. If the message received within the pre-set time period is not a next tag request or a re-display request but an end of data acknowledgement message, the mobile tag communication application 142a identifies all data has been successfully read and ends its processing by releasing the processor and display for other applications.

As discussed further below, re-display instructions may result from various causes, for example glare or contrast. The re-display instructions may simply be to re-display the currently displayed mobile tag as is. In other examples, the re-display instructions may request display of a tag not using a designated portion of the display or certain character locations in the tag depending on design choice. A display may have designated quadrants for example, and one quadrant is to be avoided. The tag may have to be displayed in parts over time which is stitched by the image processing software 164 at the request of the mobile device mobile tag communication application 142b. In other examples, data displayed on a certain designated portion of the display may be requested to be redundantly encoded in the tag so it appears elsewhere on a readable portion of the display. Responsive to receiving the re-display instructions, in step 468, application 142a causes the currently displayed mobile tag to be re-displayed in accordance with the received re-display instructions and returns to step 462.

In the examples described above, the positioning of the image sensor or camera 168 and illuminator 170 with respect to a display and photodetetector of another computer device displaying a mobile tag is not automatically controlled. A user is involved. There may be slight motion of the user hand or a user may get interrupted and move the devices out of alignment. Besides motion to one side or the other, the user may be moving the device or devices so that the distance between them and hence, the scale of the image data changes. Additionally, the mobile tag is being read off a display, some examples of which are a liquid crystal display (LCD) or a light emitting diode (LED) display, which contributes its own brightness and contrast in addition to that of the environment of the user. Speaking of environment, a user may be indoors, outdoors, out in very bright sunlight, or out on a moonless night. Each of these examples may cause errors in being able to identify a device which generates the mobile tag and read the data in a displayed mobile tag.

One of the first stages in being able to retrieve mobile tag data is detecting the region of the image acquired by the camera that corresponds to the display of the device displaying the mobile tag. One way to handle this problem is to detect the borders of the image and compare to borders which are defined a priori. They could be, for example, the stored actual borders of the display in the watch based examples shown in FIGS. 2A and 2B. Object detection software or pattern recognition by the image processing software 164 may be used to identify the display area. The captured image data may be scaled, rotated and translated to see if a match with a reference image of the device (e.g. 120) displaying the tag may be obtained. Another way to address this problem is to use some special symbols located on the corners of the region of interest, which is display 128 in the illustrated examples above, which is similar to the case of QR code detection. For example, the three large corner squares in a QR code can be identified and scale, rotation and perspective or orientation of the tag can be identified. This way also provides the advantage of indicating a level of brightness expected from the characters to be recognized. Another advantage of this way is that it is possible to use Haar like features for the detection of the special symbols. Haar-like features can also be used for identifying different regions in the image and region of interest of display 128.

Before character identification within the mobile tag, adjustments to the image data may be performed by the image processing software 162 or the mobile tag communication application 142b based on the identified corners and/or borders of the region of interest, e.g. display 128. Adjustment for perspective and rotation correction may be performed first based on dimensions data stored for the display 128 or a region of interest thereon. If the region of interest is a square or rectangle, the dimensions data indicates what the distance and relative positions are between the corners in the image data. The distance between the corners can also identify the scale of the display 128 or other region of interest on the display from a reference image.

Real life conditions will deviate from this scenario. The software 142b, 164 executing on the mobile device may have performed correction for perspective and rotation distortion by applying an inverse perspective/rotation transformation when the exact shape, orientation and size (e.g. rectangle and square) of the undistorted region of interest is stored. The applied transformation transforms the distorted coordinates to the undistorted coordinates based on the stored corner positions and the detected corner positions. The distance between the camera and the display to be read may also be an input to the transformation to address scale differences with the size of the corresponding undistorted rectangle/square.

Once the inverse transformation is found it could be used to transform every pixel on the original image obtained from the first stage. Something to keep in mind is that this is a dynamic process since the perspective, rotation and scaling could change continuously.

As mentioned above, another challenge for this stage is the uncontrolled level of brightness as the user could activate detection indoors or outdoors under variable luminance conditions due to natural or artificial light, with or without shadows. Additionally, the reflective material on the watch could at any moment produce glare, thus partially or totally blocking the displayed data and precluding successful detection. Contrast is another parameter that needs to be varied in order to facilitate detection, given the potential wide range of brightness that may exist.

The detection of the image corners, transformation of data for perspective, rotation, and scale correction, and the identification of brightness, contrast and glare are continuously performed during a tag transfer session between the devices 128 in order to provide a base-line of readiness for subsequent image adjustment and character identification.

If the detection of the region of interest in image data process in the first stage used special symbols on the corners of the display, then brightness and contrast variations were used and identified as part of the detection process. The levels of brightness and contrast identified in the detection of the special symbols can be used in a third stage to perform character recognition within a 2D bar code or other type of mobile tag.

A second stage of adjustment of image data includes identification of un-usable portions of a display. Glare is still a potential problem for the next stage of character identification since glare could block portions of the inner image region even when the corners have been successfully detected. The image processing software 164 may identify one or more portions of the displayed data affected by glare and adjust the brightness and contrast of the image data. The mobile tag communication application 142b can interface with the image processing software 164 to identify if the adjusted image data was successfully read or not. Depending on the aggressiveness of the glare it may not be possible to recover the character by performing further brightness/contrast adjustment, e.g. no more adjustment levels available to the image processing software 164 after a number of unsuccessful reads. The mobile tag communication application 142b may then send re-display instructions using the illuminator 170 indicating that the data in the identified glare portions redundantly coded elsewhere in a tag to display on another portion of the display from which data has been successfully read. Besides providing redundant information that would allow acquiring the data on different parts of the display, (allowing the data to be shown in areas not affected by the glare), another solution is to send re-display instructions which designate portions of the display as un-usable and requesting keeping display of data for transfer to the unaffected portions.

Aspects of the camera may also prevent or cause errors in detection of the display to be read or character recognition within a tag. Variation in focus is an example. An incorrect focus may be perceived as a blurred image, thus presenting an obstacle for detection and delaying data transfer. Continuous detection of the image corners may signal when a correct focus has been achieved.

Received images may also be down-sampled by the image processing software 164 since the image resolution obtained from the camera is likely several times higher than a typical resolution used to perform detection of a region of interest and character identification within a tag.

Additionally, due to varying luminance conditions it may be possible that some portions of the image get distorted or blurred even precluding detection of the special symbols of the region of interest, e.g. the corners of the rectangle or square of a tag including special handshake characters displayed on the display 128. The varying luminance conditions may also preclude the identification of characters even though the corners are successfully detected. Similar solutions as per glare may be employed by the image processing application 164 and the mobile tag communication application 142a, 142b executing on both devices by identifying one or more legible (readable) regions of the image (similarly as what is mentioned for glare above) and adjusting character presentation to display in these readable areas.

Once the region of interest is defined in image data and image adjustments made, a third stage of character identification or character recognition can proceed. In many embodiments, the characters are identified as binary values. The mobile tag communication application 142b or a mobile tag reader application it interfaces with may transform the acquired image to gray-levels first, and then to black and white levels or straight to the black and white levels. A threshold intensity value is applied to each pixel in order to define it as a black pixel or a white pixel. In many examples, the threshold value is set dependent upon the brightness level identified in the ongoing processing of stage 1.

The image data in the region of interest may be processed starting with the upper left corner and shifting by a pre-established number of pixels in order to find the first character. Small errors in previous stages can put the character in a different position from the one expected. Therefore a certain amount of searching may be performed at this point in order to obtain the character. Movements causing even small rotations, and changes in scale and perspective may result in increased or reduced character sizes. There are several methods that can be used for identification. For example, one using eigenvalues may be used. As previously mentioned, the display and image capture of a known sequence of characters in an initialization stage of the communication handshake protocol assists in identifying the image distortions and their causes.

Additional characters could be identified in a similar way by shifting from the upper left corner towards other locations where these characters are expected to be found (i.e., second, third, fourth character, etc). When recognizing additional characters some tolerance for shifting/rotation/scaling may be provided. In some examples, the software performing the character or symbol recognition for the tag can apply the corrections made for the first character for the remaining characters.

Although relying on user positioning and support of at least one of the computer devices may increase the prevalence of some distortions in the image data, a user can also be an asset for removing or lessening the sources of the distortions. For example, the mobile tag communication application 142b can provide visual indicators of the identified problems, and positioning hints. For example, if glare spots have been identified, a simple text message display of "Glare is preventing data read" informs the user, and the user can move the one or more devices to a different position with less sources of reflected light. A user can usually see glare on the display and identify when positioning has removed the glare using human sight. Additionally, an image of the display 128 with an overlay of outlines of the identified glare spots may be displayed with text requesting repositioning of one or both devices. For perspective, rotation, and scale distortions, based on the transforms for correction, directions and distance in which to move the sensing device 120 may be identified and filled in to variable positions of a prestored message for display on the device or as audio output. For example, the mobile device 150 identifies that it has read the 2D barcode correctly by doing a check sum. If it has not read it due to a camera focus issue, then the mobile device 150 alerts the user who can reposition the phone to make sure the focus of the device camera is right. Additionally, the visual aids such as the outline in FIG. 2A may help the user keep the devices in a good position range for reading. Other embodiments may also include one or more structures which position the devices to reduce image distortions and thus increase the speed of the transfer of data.

FIGS. 6, 7A, 7B and 7C illustrate examples of fixtures on which a mobile device with camera can be placed or provides support for a user holding the device. The fixtures cut down on perspective and scaling errors to increase data transfer efficiency.

Figure 6:
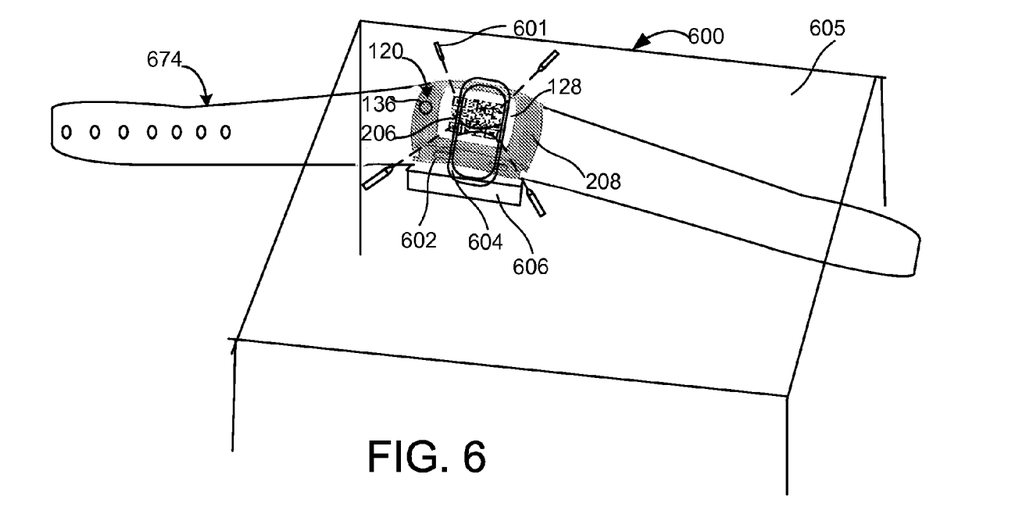
FIG. 6 illustrates an example of an alignment fixture in which a user wearable computer device is placed at a designated position and which provides a support with holes aligned with a designated position for a hand held mobile device with an image sensor and an illuminator.

FIG. 6 illustrates an example of an alignment fixture 600 in which a user wearable computer device 120 is placed at a designated position 606 and which provides a support structure 605 with one or more holes 604 aligned with the designated position 606 for a hand held mobile device with an image sensor and an illuminator. The device 120 in this example is in a wrist watch form factor with a watch portion 208 in a wristband 674. The wristband 674 is an example of a wrist wearable support structure. A user places the watch portion 208 on the designated position of a pedestal 606 which is sized for the watch portion in this example. A mobile device like a smartphone, like the one illustrated in FIGS. 3A and 3B is placed on support 605 over one or more holes to be aligned with the pedestal 606 and watch display 128 it supports. In this embodiment, the one or more holes are embodied as a hole 604 which has a raised edge or lip to fit a groove around the camera aperture 11 and illuminator 170 commonly found in some models of smartphones to help secure the smartphone to the fixture 600. The user places the watch inside the fixture, and then turns on the LEDs 601 which direct light at the pedestal area to improve the readability of the mobile tag, a QR code 206 in this example, by increasing the contrast, and avoiding reflection on the LCD display 128. Four light emitting diodes (LEDs) are illustrated but only one is labeled 601 to avoid overcrowding the drawing. Particularly, in a case where a grooved or other structure for securing the mobile device in place over the hole is not provided, a message can be output to the user when the devices are positioned correctly. As in FIG. 2B, a message saying "Aligned" can be displayed, so the user can release hold of the phone and let it rest on supporting wall 605 of the structure 600 during data transfer. The fixture 600 drastically reduces image scale problems due to varying distance between the devices. Perspective, rotation, and glare distortions are also greatly reduced.

Figure 7A:
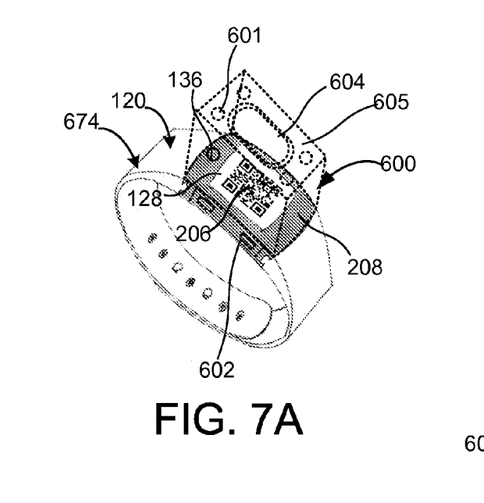
FIGS. 7A, 7B and 7C illustrate another example of an alignment fixture which attaches and detaches from a wristband display version of a user wearable computer device.
Figure 7B:
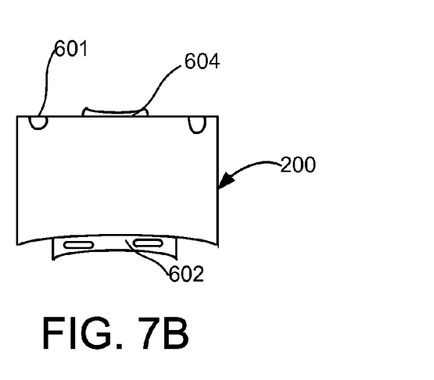
Figure 7C:
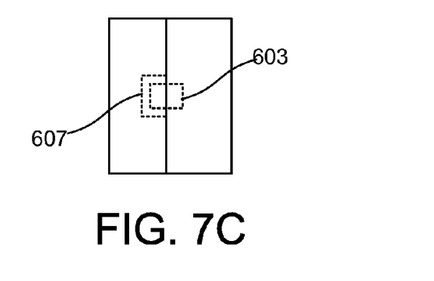

FIGS. 7A, 7B and 7C illustrate another example of an alignment fixture 600 with a support structure 605 including a hole 604 which attaches and detaches from a wristband display version of a user wearable computer device. In this example, another version of structure 600 fits to the watch 208 and can be attached when a user wears the wrist watch biometric sensing device 120. The sides conform around the buttons 602 on the sides as shown in FIGS. 7A and 7B. FIG. 7C shows a fastener on the bottom in which one side 603 snaps into the other 607. This version also has the raised rim, edge or lip for a perimeter to fit around a grooved region surrounding a camera aperture and a camera illuminator which helps the user hold the smartphone camera aperture 11 and illuminator 170 in place. If a small power source is available or an attachment to a battery of the sensing device 120 is included in the structure, the LEDs 601 may also be present for improving readability by increasing contact. Fixtures or structures provide a known distance for scaling and a fixed perspective.

The foregoing detailed description has been presented for purposes of illustration and description. It is not intended to be exhaustive or limiting to the precise form disclosed. Many modifications and variations are possible in light of the above teaching. The described embodiments were chosen in order to best explain the principles of the disclosed technology and its practical application, to thereby enable others skilled in the art to best utilize the technology in various embodiments and with various modifications as are suited to the particular use contemplated.

What is claimed is:

1. A user wearable biometric sensing computer device for communicating biometric data to a mobile computer device comprising:
   a display;
   a processor communicatively coupled to the display;
   one or more biometric sensing units communicatively coupled to the processor for generating biometric data;
   a memory accessible by the processor for storing software and the biometric data;
   a photodetector unit communicatively coupled to the processor captures one or more sequences of light flashes, and converts the one or more sequences of light flashes into digital data, and stores the digital data in the memory;
   the processor identifying one or more messages in the digital data based on a communication handshake protocol for the one or more sequences of light flashes;
   the processor controlling display of the biometric data formatted in one or more mobile tags in accordance with a mobile tag code on the display based on the one or more messages identified in the one or more sequences of light flashes; and
      a user wearable support structure supporting the processor, the display, the memory, the one or more biometric sensing units and the photodetector unit.

2. The user wearable device of claim 1 wherein the user wearable support structure is a wrist wearable support structure and the one or more biometric sensing units includes a heart rate monitor.

3. The user wearable device of claim 1 wherein the mobile tag code is a two dimensional bar code.

4. The user wearable device of claim 1 wherein the mobile tag code is a QR code.

5. The user wearable device of claim 2 further comprising a watch display and an attachable fixture which fits around and above the watch display, the fixture having an opening with a perimeter which fits around a grooved region surrounding a camera aperture and a camera illuminator of a hand held mobile computer device.

6. A system for transferring one or more mobile tags using a light based communication handshake protocol comprising:
   a mobile device including a processor, a memory storing software and data and being accessible by the processor, an image sensor and an illuminator, the processor being communicatively coupled to the image sensor and the illuminator;
   the mobile device further comprising one or more user input devices;
   the processor under control of the software receives user input from the one or more user input devices indicating a request for transfer of data from another computer device and turns the image sensor on and causes the illuminator to generate a sequence of light flashes indicating a message requesting transfer of the data in accordance with a communication handshake protocol using one or more sequences of light flashes;
      the processor under control of the software identifies a mobile tag in image data being captured by the image sensor, and extracts data encoded in the mobile tag; and
      responsive to the data extracted from the mobile tag indicating there is more data to be transferred, the processor causes the illuminator to generate a sequence of light flashes indicating a message to display another mobile tag encoded with data.

7. The system of claim 6 wherein the illuminator is a camera flash.

8. The system of claim 6 wherein the other computer device is a user wearable biometric sensing computer device including a display for displaying the mobile tag, a photodetector unit which detects the sequence of light flashes, converts the light flashes to digital data, and stores the digital data in a memory, and a processor having access to the memory and being communicatively coupled to the photodetector unit and the display.

9. The system of claim 8 further comprising:
   the mobile device further comprising a display communicatively coupled to the processor which display displays a field of view of the image sensor; and
   the processor under control of the software causes the display to display a visual aid indicating the mobile tag is within the field of view of the image sensor.

10. The system of claim 8 further comprising:
    the mobile device further comprising a display communicatively coupled to the processor which display displays a field of view of the image sensor;
    the processor causing the display to display an image of an outline of the user wearable biometric sensing computer device; and
    responsive to the image of the outline matching a perimeter of the user wearable biometric sensing computer device in image data being captured by the image sensor, displaying a visual aid indicating the image sensor is aligned for data capture with the display of the user wearable biometric sensing computer device.

11. The system of claim 9 further comprising the processor under control of the software displaying a notification on the display that the mobile tag is unreadable.

12. The system of claim 6 wherein the mobile computer device is a hand held mobile computer device having an aperture for the image sensor and the illuminator on a same exterior side, and the system further comprises:
    a fixture having an inside portion including a designated position at which the display of the user wearable biometric sensing computer device is placed, the fixture comprising a support structure opposite the display of the user wearable biometric sensing computer device providing a support against which the same exterior side of the hand held mobile computer device is positioned, the support structure having one or more holes over which the aperture of the image sensor and the illuminator can be placed.

13. A method for transferring one or more mobile tags using a light based communication handshake protocol comprising:
- capturing image data of an electronically displayed mobile tag with an image sensor of a mobile computer device;
- identifying a successful read of data encoded in the mobile tag;
- identifying from the data encoded in the mobile tag whether the mobile tag is the last mobile tag of data in a series of mobile tags;
- responsive to the mobile tag not being the last mobile tag of data in the series, generating a sequence of light flashes with an illuminator of the mobile computer device indicating to display a next mobile tag in accordance with a communication handshake protocol; and
- responsive to the mobile tag being the last mobile tag of data in the series, updating the display of the mobile computer device to indicate an end of data transfer for the user.

14. The method of claim 13 further comprising:
- generating a sequence of light flashes indicating an end of data transfer acknowledgement message.

15. The method of claim 13 further comprising:
- communicating one or more mobile tags or the data encoded in the one or more mobile tags over a network to a third computer system; and
- sending a notification indicating the end of the data transfer to the third computer system over the network.

16. The method of claim 13 further comprising:
- receiving user input indicating a request to upload mobile tag data from a user wearable computer device;
- automatically turning on an image sensor of the mobile device for capturing image data;
- generating one or more sequences of light flashes by an illuminator of the mobile device indicating a request to the user wearable computer device to start displaying one or more mobile tags in accordance with the communication handshake protocol;
- determining whether a mobile tag of data has been successfully read within a pre-set time period; and
- responsive to an unsuccessful read, outputting a notification by the mobile device in at least one of audio data or visual data indicating an unsuccessful read of the mobile tag data.

17. The method of claim 16 wherein responsive to an unsuccessful read, outputting a notification by the mobile device in at least one of audio data or visual data indicating an unsuccessful read of the mobile tag data further comprising:
- outputting one or more positioning hints for the user.

18. The method of claim 16 further comprising:
- displaying one or more visual aids for assisting the user in positioning a user wearable computer device in a field of view of the image sensor of the mobile device.

19. The method of claim 16 further comprising:
- encoding data in one or more mobile tags with a last mobile tag indicating an end of data;
- detecting the one or more sequences of light flashes by a photodetector unit of the user wearable computer device and converting the one or more sequences of light flashes to digital data in accordance with a communication handshake protocol;
- determining whether the digital data indicates a start request for data transfer within a pre-set time period;
- responsive to the start request not being indicating, ending processing for transferring mobile tag data;
- responsive to the start request being indicated, displaying an initial mobile tag;
- determining whether a sequence of light flashes indicating a next tag request in accordance with the communication handshake protocol has been received with a pre-set time period; and
- responsive to the next tag request being indicated, display the next mobile tag.

20. The method of claim 19 wherein the data in the one or more mobile tags is biometric data.

* * * * *